United States Patent
Motohara

(10) Patent No.: US 9,385,249 B2
(45) Date of Patent: Jul. 5, 2016

(54) OPTICAL ELEMENT MODULE, OPTICAL TRANSMISSION MODULE, AND METHOD OF MANUFACTURING OPTICAL TRANSMISSION MODULE

(71) Applicant: OLYMPUS CORPORATION, Tokyo (JP)

(72) Inventor: Hiroyuki Motohara, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/104,345

(22) Filed: Dec. 12, 2013

(65) Prior Publication Data

US 2014/0097459 A1 Apr. 10, 2014

Related U.S. Application Data

(63) Continuation of application No. PCT/JP2012/068108, filed on Jul. 17, 2012.

(30) Foreign Application Priority Data

Jul. 21, 2011 (JP) ................. 2011-159847

(51) Int. Cl.
*H01L 31/0232* (2014.01)
*H01L 33/58* (2010.01)
(Continued)

(52) U.S. Cl.
CPC ........ *H01L 31/02325* (2013.01); *G02B 6/3644* (2013.01); *G02B 6/4202* (2013.01);
(Continued)

(58) Field of Classification Search
CPC . H01S 5/18327; H01S 5/022; H01S 31/0232; H01S 33/58; G02B 6/12

USPC ............................................. 257/98; 372/38
See application file for complete search history.

(56) References Cited

U.S. PATENT DOCUMENTS 6,243,508 B1 6/2001 Jewell et al.
6,877,911 B2* 4/2005 Ide ..................... G02B 6/422
385/88

(Continued)

FOREIGN PATENT DOCUMENTS

JP S59-4509 U 1/1984
JP S63-107408 U 7/1988
(Continued)

OTHER PUBLICATIONS

.JP2009047937_trans_en.pdf is an english attachment of FP JP2009047937A.*
(Continued)

*Primary Examiner* — Peniel M Gumedzoe
(74) *Attorney, Agent, or Firm* — Scully, Scott, Murphy & Presser, P.C.

(57) ABSTRACT

An optical element module includes an optical element having a light receiving unit configured to input an optical signal or a light emitting unit configured to output an optical signal, a board on which the optical element is mounted, and a guide holding member that has a through hole into which an optical fiber is configured to be inserted for inputting and outputting the optical signal to or from the light receiving unit or the light emitting unit of the optical element, and is mounted and arranged to be aligned with the optical element in a thickness direction of the board. The through hole has a cylindrical shape and has substantially the same diameter as an outer diameter of the optical fiber. A diameter of the light receiving unit or the light emitting unit is smaller than that of the optical fiber.

9 Claims, 9 Drawing Sheets

(51) Int. Cl.
 H01S 5/022 (2006.01)
 G02B 6/36 (2006.01)
 G02B 6/42 (2006.01)
 H01S 5/183 (2006.01)

(52) U.S. Cl.
 CPC .............. G02B6/4257 (2013.01); H01L 33/58 (2013.01); H01S 5/02252 (2013.01); *G02B 6/4239* (2013.01); *H01L 2224/13* (2013.01); *H01L 2224/45144* (2013.01); *H01L 2224/48091* (2013.01); *H01L 2224/48465* (2013.01); *H01L 2224/73265* (2013.01); H01S 5/02284 (2013.01); H01S 5/183 (2013.01)

(56) References Cited

U.S. PATENT DOCUMENTS

| | | | |
|---|---|---|---|
| 2002/0118924 A1* | 8/2002 | Murata | G02B 6/4202 385/52 |
| 2002/0159719 A1 | 10/2002 | Ide et al. | |
| 2006/0039658 A1* | 2/2006 | Furuyama et al. | 385/90 |
| 2007/0278666 A1* | 12/2007 | Garcia et al. | 257/707 |
| 2008/0285303 A1* | 11/2008 | Matsui et al. | 362/580 |
| 2009/0136237 A1* | 5/2009 | Martini et al. | 398/141 |
| 2009/0186305 A1* | 7/2009 | Hodono | 430/321 |
| 2013/0209038 A1* | 8/2013 | Pommer et al. | 385/76 |

FOREIGN PATENT DOCUMENTS

| | | | |
|---|---|---|---|
| JP | 09-090175 A | 4/1997 | |
| JP | 2002-252430 A | 9/2002 | |
| JP | 2005-208107 A | 8/2005 | |
| JP | 2005-286284 A | 10/2005 | |
| JP | 2006-145787 A | 6/2006 | |
| JP | 2007-316548 A | 12/2007 | |
| JP | 2009-047937 A | 3/2009 | |
| JP | 2009047937 A * | 3/2009 | G02B 6/42 |
| JP | 2009-206158 A | 9/2009 | |
| JP | 2010-048940 A | 3/2010 | |

OTHER PUBLICATIONS

English Abstract only of EP 1 816 497 A1 dated Aug. 8, 2007.
International Seaerch Report dated Aug. 14, 2012 issued in PCT/JP2012/068108.
Extended Supplementary European Search Report dated Feb. 25, 2015 from related European Application No. 12 81 4657.8.
Japanese Office Action dated Jun. 2, 2015 from related Japanese Patent Application No. 2011-159847, together with an English language translation.

* cited by examiner

OPTICAL ELEMENT MODULE, OPTICAL TRANSMISSION MODULE, AND METHOD OF MANUFACTURING OPTICAL TRANSMISSION MODULE

CROSS-REFERENCE TO RELATED APPLICATION(S)

This application is a continuation of PCT international application Ser. No. PCT/JP2012/068108 filed on Jul. 17, 2012 which designates the United States, incorporated herein by reference, and which claims the benefit of priority from Japanese Patent Applications No. 2011-159847, filed on Jul. 21, 2011, incorporated herein by reference.

BACKGROUND

1. Technical Field

The disclosure relates to an optical element module, an optical transmission module, and a method of manufacturing the optical transmission module.

2. Related Art

In related art, a medical endoscope enables observation of a lesion part by inserting an insertion unit of the endoscope deeply into a human body, and enables an examination and treatment of the human body by further using a treatment tool together as necessary. As such an endoscope, there is an endoscope having an imaging apparatus incorporating an imaging device such as a CCD at a distal end of the insertion unit. In recent years, an imaging device with a high pixel number, which enables a clearer image observation, has been developed, and use of such an imaging device having a high pixel number in the endoscope has been considered. In a case where an imaging device having a high pixel number is used in an endoscope, in order to transmit a signal at a high speed between the imaging device and a signal processing device, it is necessary to incorporate an optical transmission module in an endoscope. To reduce a burden on a patient and secure a visual field for observation, it is desirable that an outer diameter and a length of the distal end portion of the insertion unit of an endoscope be as small as possible. Accordingly, a width and a length of an optical element module, which is a hard portion constituting an optical transmission module to be incorporated in an endoscope, be also as small as possible.

As a technology related to a photoelectric conversion element circuit for conversion between an optical signal and an electric signal, an optical communication module is disclosed. In the optical communication module, one end of an optical fiber is inserted into and fixed to a ferrule, and the ferrule is fixed to a board having a photoelectric conversion element and a holding member mounted on different surfaces of the board by being inserted into a through hole formed in the holding member. The board includes a through hole to which an end face of the optical fiber fixed by the ferrule and the holding member is exposed, and an optical communication is performed via the through hole (see for example, Japanese Laid-open Patent Publication No. 09-090175).

SUMMARY

In accordance with some embodiments, an optical element module, an optical transmission module, and a method of manufacturing the optical transmission module are provided.

In some embodiments, an optical element module includes an optical element having a light receiving unit configured to input an optical signal or a light emitting unit configured to output an optical signal, a board on which the optical element is mounted, and a guide holding member that has a through hole into which an optical fiber is configured to be inserted for inputting and outputting the optical signal to or from the light receiving unit or the light emitting unit of the optical element, and is mounted and arranged to be aligned with the optical element in a thickness direction of the board. The through hole has a cylindrical shape and has substantially the same diameter as an outer diameter of the optical fiber. A diameter of the light receiving unit or the light emitting unit is smaller than that of the optical fiber.

In some embodiments, an optical transmission module using the optical element module includes an optical fiber inserted into the through hole. The optical fiber is joined to the guide holding member by optically aligning one end face of the optical fiber with the light emitting unit or the light receiving unit of the optical element.

In some embodiments, a method of manufacturing an optical transmission module is provided. The optical transmission module includes an optical element having a light receiving unit for inputting an optical signal or a light emitting unit for outputting an optical signal, a board on which the optical element is mounted, and an optical fiber for inputting or outputting the optical signal to or from the optical element. The method includes: mounting the optical element on a surface of the board; mounting a guide holding member having a through hole which has a cylindrical shape and has substantially the same diameter as an outer diameter of the optical fiber, on the board after mounting the optical element on the board, by aligning a center of the light receiving unit or the light emitting unit with a center of the through hole and by arranging the guide holding member to be aligned with the optical element in a thickness direction of the board; inserting the optical fiber into the through hole; adjusting a distance between an end face of the optical fiber and the light receiving unit or the light emitting unit and optically aligning the end face of the optical fiber with the light emitting unit or the light receiving unit; and joining the optical fiber to the guide holding member.

The above and other objects, features, advantages and technical and industrial significance of this invention will be better understood by reading the following detailed description of presently preferred embodiments of the invention, when considered in connection with the accompanying drawings.

DETAILED DESCRIPTION

Figure 1:
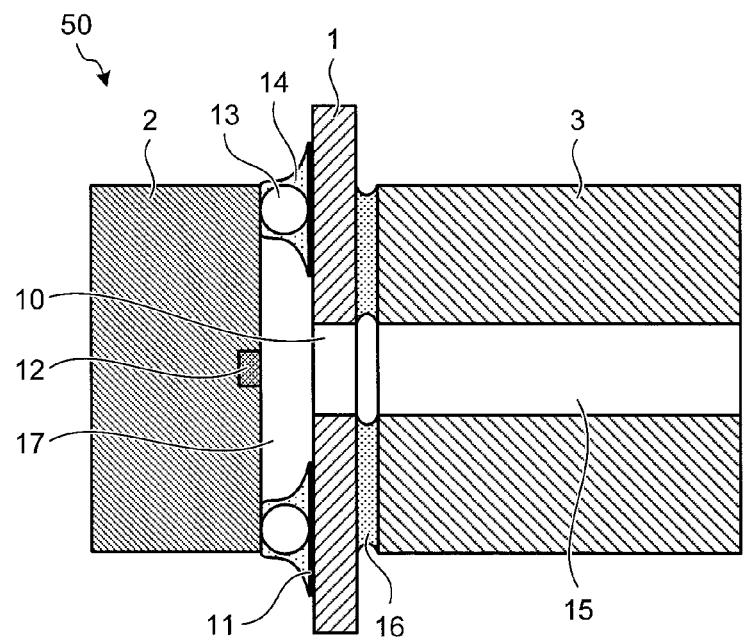
FIG. 1 is a cross-sectional view of an optical element module according to a first embodiment of the present invention.

Hereinafter, embodiments for carrying out the present invention (hereinafter, referred to as "embodiments") will be described with reference to the attached drawings. Note that these embodiments do not intend to limit the present invention. In the drawings, the same elements are denoted with the same reference numerals. It should be noted that the drawings are schematic, and a relationship between the thickness and the width of each member, a ratio between each member, and the like may be different from reality. Also between the drawings, there may be a part containing a difference in a relationship or a ratio between each size.

First Embodiment

Figure 2:
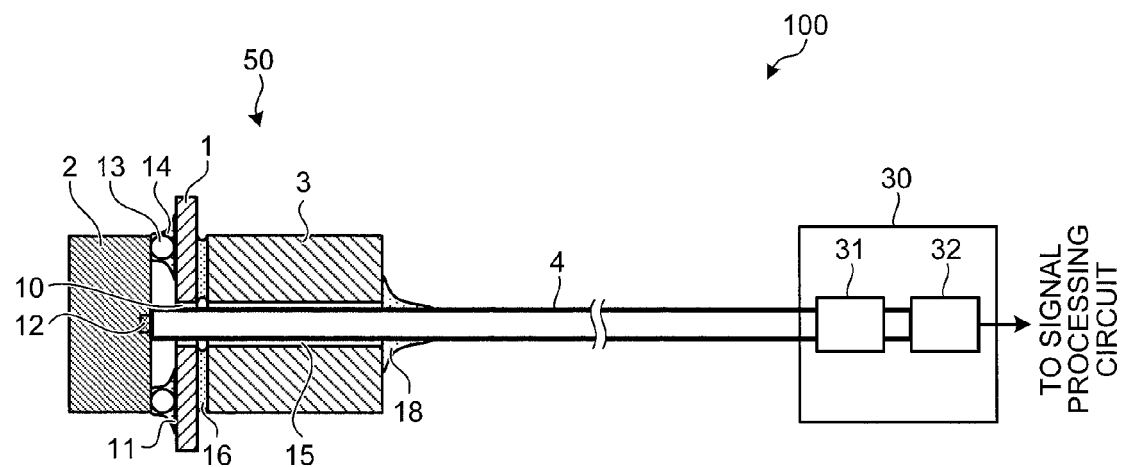
FIG. 2 is a cross-sectional view of an optical transmission module using the optical element module according to FIG. 1.
Figure 3:
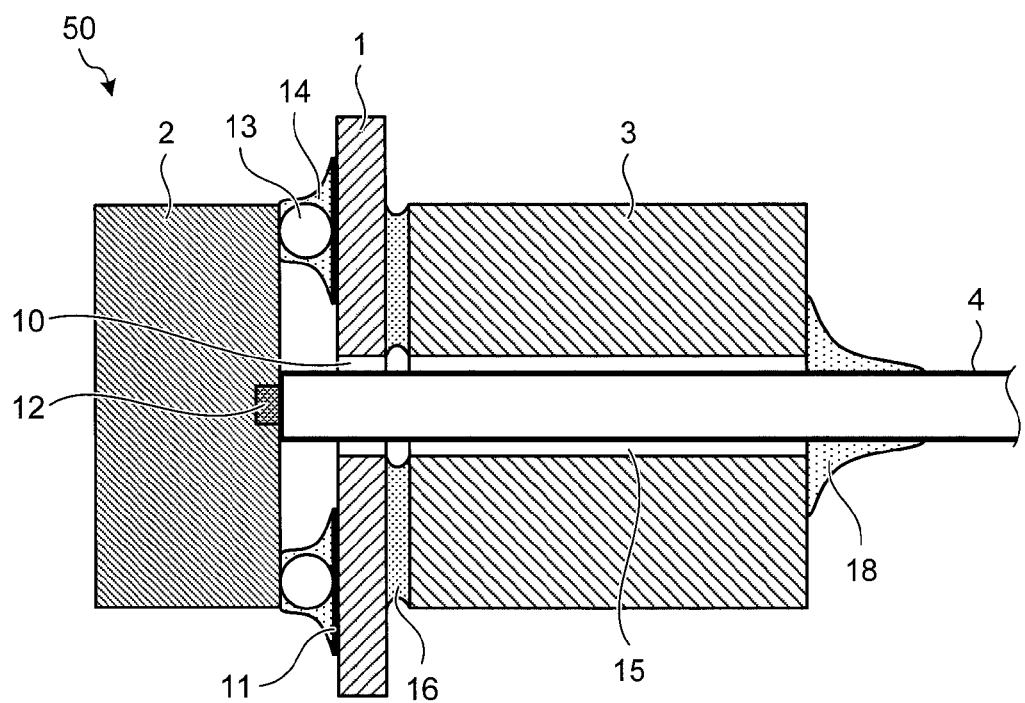
FIG. 3 is a cross-sectional view of a fixing portion between the optical element module and an optical fiber of the optical transmission module according to FIG. 2.
Figure 4:
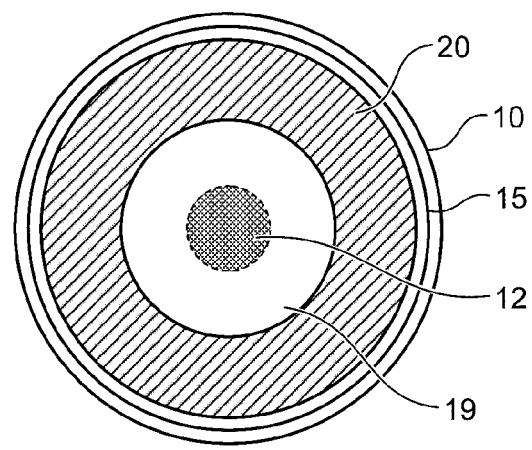
FIG. 4 is a plan view of a hole in a board of the optical transmission module according to FIG. 2 viewed from a surface emitting laser side.

FIG. 1 is a cross-sectional view of an optical element module 50 according to a first embodiment of the present invention. FIG. 2 is a cross-sectional view of an optical transmission module 100 using the optical element module 50 in FIG. 1. FIG. 3 is a cross-sectional view of a fixing portion of the optical element module 50 and an optical fiber 4 of the optical transmission module 100 in FIG. 2. FIG. 4 is a plan view of a hole 10 of a board 1 of the optical transmission module 100 in FIG. 2 viewed from a surface emitting laser 2 side.

The optical transmission module 100 according to the first embodiment of the present invention includes the optical element module 50, the optical fiber 4 for transmitting an optical signal, and an optical element module 30 for transmitting an optical signal to the optical element module 50 or receiving an optical signal from the optical element module 50. The optical element module 50 and the optical element module 30 function as a transmitting module or a receiving module, and when one of the modules functions as the transmitting module, the other functions as the receiving module. In the first embodiment, reference will be made to a case where the optical element module 50 serves as the transmitting module, and the optical element module 30 serves as the receiving module.

The optical element module 50 includes the board 1, the surface emitting laser 2, which is a light emitting element mounted on the board 1, and a guide holding member 3 mounted on a surface opposite of a surface on which the surface emitting laser 2 is mounted of the board 1. The optical fiber 4 is joined to the optical element module 50, and an optical element module 30 is connected to another end face of the optical fiber 4. The optical element module 30 includes a light receiving element 31, which is a photodiode (hereinafter, referred to as PD) that converts light into an electrical current by receiving an optical signal output from the surface emitting laser 2, and a transimpedance amplifier 32 (hereinafter, referred to as TIA 32), which performs impedance conversion on this converted electric signal, amplifies it, and outputs it as a voltage signal. The optical element module 30 is further coupled to an external signal processing circuit through TIA 32.

In the optical element module 50, the guide holding member 3 and the surface emitting laser 2 are mounted and arranged on different surfaces of the board 1 to be aligned with each other in a thickness direction of the board 1. As the board 1, an FPC board, a ceramic board, a glass epoxy board, a glass board, an Si board, and the like are used. On the board 1, a connection electrode 11 is formed, and an electric signal is transmitted to the surface emitting laser 2 through the connection electrode 11. The surface emitting laser 2 is of a flip-chip type in which a light emitting unit 12 thereof is mounted on the board 1 so as to face the board 1. When mounting the surface emitting laser 2 on the board 1, an Au bump 13 is formed on the surface emitting laser 2, which is joined to a connection electrode 11 on the board 1 by ultrasonic, for example. In the mounting, an adhesive 14 such as an underfill material or a sidefill material is put into a joining portion, and then the adhesive 14 is hardened. Alternatively, without using Au bump, the mounting can be performed by printing a solder paste or the like on the board 1, disposing the surface emitting laser 2 thereon, and then melting the solder by reflow soldering and the like. Alternatively, the mounting can be performed by forming a solder bump on the surface emitting laser 2, disposing it on the connection electrode 11 on the board 1 by a mounting device, and melting the solder.

The guide holding member 3 has a through hole 15 having a cylindrical shape and substantially the same diameter as an outer diameter of the optical fiber 4 to be held. Mounting of the guide holding member 3 on the board 1 is performed by, for example, after applying an adhesive 16 on the mounting surface of the board 1, mounting the guide holding member 3 on the adhesive 16 by a device such as a bonder, and hardening the adhesive 16. The through hole 15 may also be a prism shape in addition to a cylindrical shape as long as it can hold the optical fiber 4 with an inner surface thereof. A material of the guide holding member 3 may be ceramic, Si, glass, metal such as SUS, and the like.

The board 1 has the hole 10 for transmitting an optical signal to and receiving it from the surface emitting laser 2. An inner diameter of the hole 10 is formed to be the same as or slightly larger than an inner diameter of the through hole 15. The optical fiber 4, which is inserted into the through hole 15 of the guide holding member 3 and is mounted on the optical element module 50, receives the light emitted from the light emitting unit 12 of the surface emitting laser 2 through the hole 10.

Mounting of the surface emitting laser 2 on the board 1 is performed such that the hole 10 is positioned right below the light emitting unit 12 by aligning a center of the light emitting unit 12 of the surface emitting laser 2 with a center of the hole 10 by using a dual-view optical system. Furthermore, mounting of the guide holding member 3 on the board 1 is performed by aligning the center of the light emitting unit 12 of the surface emitting laser 2 with a center of the through hole 15 by using a dual-view optical system.

Mounting of the optical fiber 4 on the optical element module 50 is performed via the through hole 15. Between an end face of the through hole 15 on the surface emitting laser 2 side and the light emitting unit 12, the optical element module 50 has a hole 10 and a space 17 that enable an adjustment of a distance between an end face of the optical fiber 4 to be inserted and the light emitting unit 12. The space 17 is a space between the surface emitting laser 2 and the board 1. The optical fiber 4 is inserted into the through hole 15 to reach the vicinity of the light emitting unit 12 through the hole 10. At a position where light output from the light emitting unit 12 can be efficiently input, the optical fiber 4 is joined to the guide holding member 3 by an adhesive 18 to constitute the optical transmission module 100. Note that in a case where the optical fiber 4 is to be joined simply, it may be joined by contacting end faces of the light emitting unit 12 and the optical fiber 4.

The optical fiber 4 includes a core 19 for transmitting light and a cladding 20 provided on an outer periphery of the core 19, and is configured to be inserted into the through hole 15 without being covered with a jacket such as of resin. Herein, an outer diameter of the optical fiber 4 shall be a diameter of the cladding 20.

In a case where a multimode optical fiber is used as the optical fiber 4, a diameter of the core 19 is about 50 μm, and that of a circular light emitting area of the light emitting unit 12 of the surface emitting laser 2 is about 20 μm. As illustrated in FIG. 4, the light emitting area of the light emitting unit 12 is within the core 19, whereby optical coupling can be performed easily.

In the optical transmission module 100 according to the first embodiment, the surface emitting laser 2 receives an electric signal from an electronic device, not illustrated, mounted on the board 1, and converts the received electric signal into an optical signal to turn the light emitting unit 12 on and off. The optical signal output from the light emitting unit 12 is input to the optical fiber 4, and the optical fiber 4 transmits the optical signal to a signal processing device and the like, not illustrated, whereby data is transmitted.

According to the optical transmission module 100 of the first embodiment, it is possible to easily position the optical fiber 4 and to hold the optical fiber 4 by using the guide holding member 3 only, thus miniaturization can be achieved. Furthermore, an optical coupling between the optical fiber 4 and the surface emitting laser 2 becomes possible without deteriorating a joining strength of the optical fiber 4. Note that in this the first embodiment, reference has been made to the optical transmission module 100 in which an optical communication is performed between the surface emitting laser 2 and the optical fiber 4; however, in an optical transmission module in which the surface emitting laser 2 is replaced with a light receiving element as the optical element as well, the positioning of the optical fiber 4 can be easily performed by using the guide holding member 3 only. Therefore, in the same way as the optical transmission module in which the surface emitting laser 2 is mounted, miniaturization can be achieved, and the optical coupling between the optical fiber 4 and the light receiving element is possible without deteriorating the joining strength of the optical fiber 4.

Second Embodiment

Figure 5:
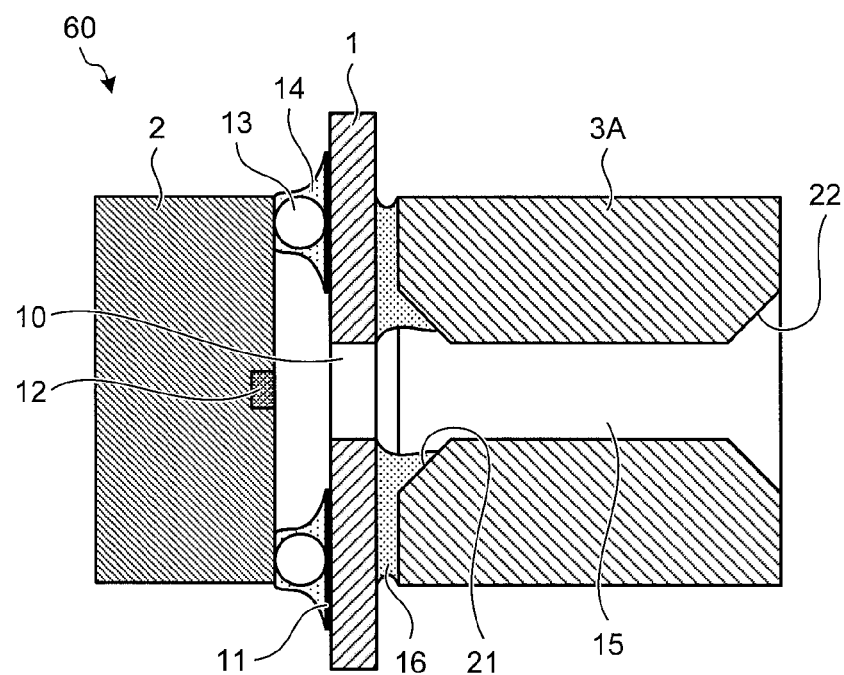
FIG. 5 is a cross-sectional view of an optical element module according to a second embodiment.
Figure 6:
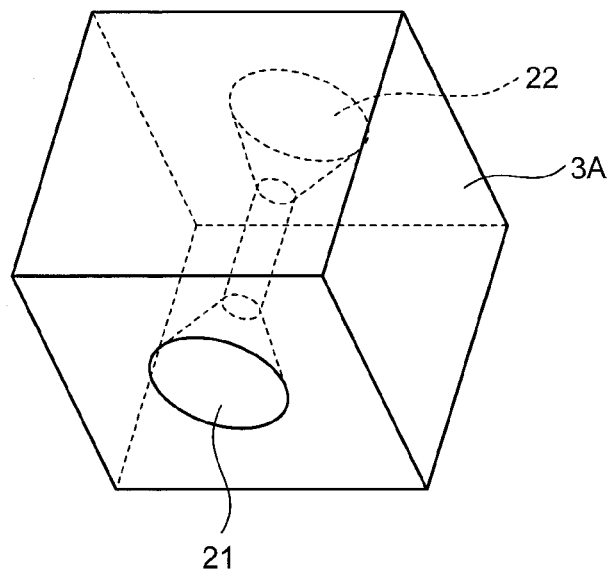
FIG. 6 is a perspective view of a guide holding member used in the second embodiment.
Figure 7:
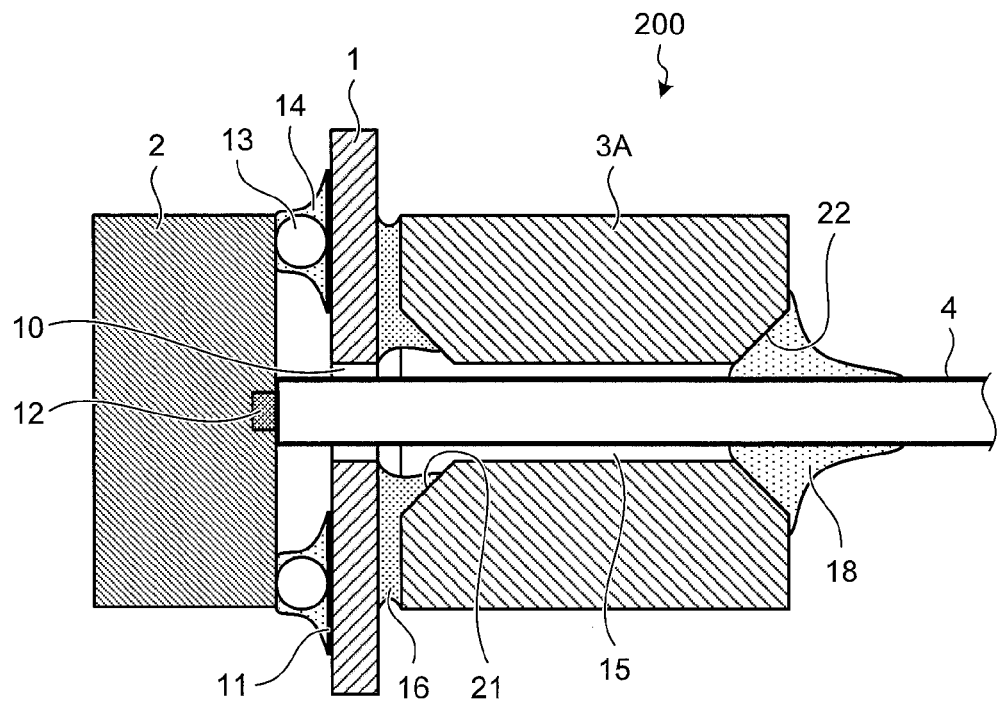
FIG. 7 is a cross-sectional view of an optical transmission module in which an optical fiber is inserted into and fixed to the optical element module according to FIG. 5.

An optical transmission module according to a second embodiment is different from the optical transmission module 100 according to the first embodiment in that tapers are formed at both ends of a through hole in a guide holding member. Hereinafter, the optical transmission module according to the second embodiment is described with reference to the drawings. FIG. 5 is a cross-sectional view of an optical element module 60 according to the second embodiment. FIG. 6 is a perspective view of a guide holding member 3A used in the second embodiment. FIG. 7 is a cross-sectional view of an optical transmission module 200 in which an optical fiber 4 is inserted into and fixed to the optical element module 60 in FIG. 5. The optical transmission module 200 in FIG. 7 is formed of the optical element module 60 and the optical fiber 4, and in the same way as the optical transmission module 100 according to the first embodiment, it may be configured such that the optical element module 30 is connected to the another end face of the optical fiber 4.

The optical element module 60 according to the second embodiment has a taper 21 and a taper 22 formed at both ends of a through hole 15.

In the second embodiment, mounting of the guide holding member 3A on a board 1 is performed by, after applying an adhesive 16 on a mounting surface of the board 1, mounting the guide holding member 3A on the adhesive 16 by a device such as a bonder, and hardening the adhesive 16. For example, in a case where a supply amount of the adhesive 16 is larger than a specified amount or where a load larger than the specified amount is put during the mounting of the guide member 3A, the adhesive 16 may overflow inside a hole 10 of the board 1 and may harden. If the adhesive 16 is overflowed inside the hole 10 and is hardened, the optical fiber 4 cannot be inserted into the hole 10. By forming the taper 21 on a mounting surface side of the board 1 of the guide holding member 3A, even in a case where the supply amount is excessive, the extra adhesive 16 stays inside the taper 21 and does not protrude into the hole 10, whereby the insertion of the optical fiber 4 can be performed without any problem. Accordingly, a yield rate in manufacturing of the optical element module 60 can be improved.

Furthermore, in the second embodiment, the optical fiber 4 is inserted into the through hole 15 in which the taper 22 is formed on an insertion side to reach the vicinity of the light emitting unit 12 through the hole 10, and is joined to the guide holding member 3A by the adhesive 18 at a position where light output from the light emitting unit 12 can be efficiently input. By forming the taper 22 in the through hole 15 on an insertion side of the optical fiber 4, the insertion of the optical fiber 4 into the through hole 15 can be performed easily. Furthermore, since the optical fiber 4 and the guide holding member 3A are joined by supplying the adhesive 18 inside the taper 22, a joining area of the guide holding member 3A and the optical fiber 4 can be made larger, whereby a joining strength can be improved.

Note that it is not limited to a taper as long as the shape can prevent a protrusion of the adhesive 16 into the hole 10, can make the insertion of the optical fiber 4 into the through hole 15 easier, and can make an joining area of the guide holding member 3A and the optical fiber 4 larger. For example, it is also possible to form a cylindrical groove portion having a diameter larger than an inner diameter of the through hole 15 at both ends of the through hole 15.

Figure 8:
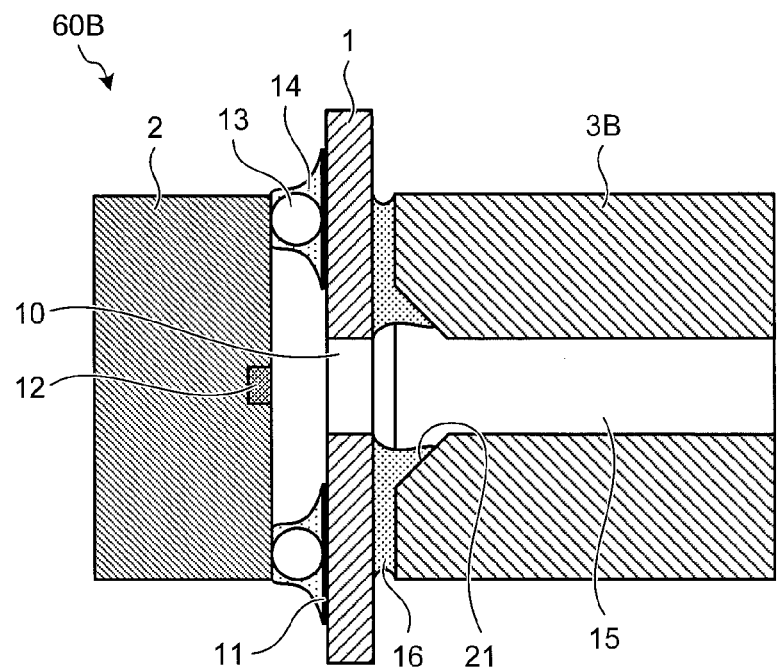
FIG. 8 is a cross-sectional view of an optical element module according to Modification 1 of the second embodiment.

As Modification 1 of the optical element module 60 according to the second embodiment, an optical element module 60B illustrated in FIG. 8 is exemplified. In the optical element module 60B according to Modification 1, the taper 21 is formed only on a side adjacent to the board 1 in the through hole 15 of a guide holding member 3B. By forming the taper 21 in the through hole 15, protrusion of the adhesive 16 into the hole 10 can be prevented, and the yield rate in manufacturing of the optical element module 60B can be improved.

Figure 9:
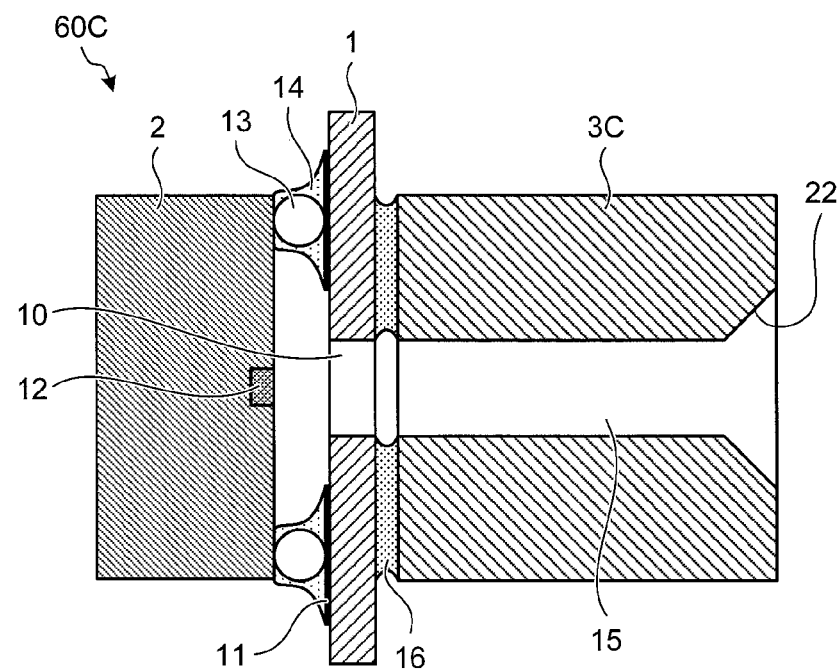
FIG. 9 is a cross-sectional view of an optical element module according to Modification 2 of the second embodiment.

Furthermore, as Modification 2 of the optical element module 60 according to the second embodiment, an optical element module 60C illustrated in FIG. 9 is exemplified. In the optical element module 60C according to Modification 2, in the through hole 15 of a guide holding member 3C, the taper 22 is formed only on a side of an insertion opening for the optical fiber 4. By forming the taper 22 in the through hole 15, not only can it function as a guide when the optical fiber 4 is inserted but also increase an adhesive area by supplying the adhesive 18 to the taper 22 when joining the optical fiber 4 and the guide holding member 3C, whereby an adhesive strength. Furthermore, the through hole 15 may have a taper shape integral from the side of an insertion opening for the optical fiber 4 to an outlet side thereof. In a case where the through hole 15 has the integral taper, it is preferable that a holding portion having substantially the same diameter as an outer diameter of the optical fiber 4 be provided on the outlet side of the optical fiber 4 so as to enable positioning without any misalignment when joining the optical fiber 4 to the guide holding member 3C.

Third Embodiment

Figure 10:
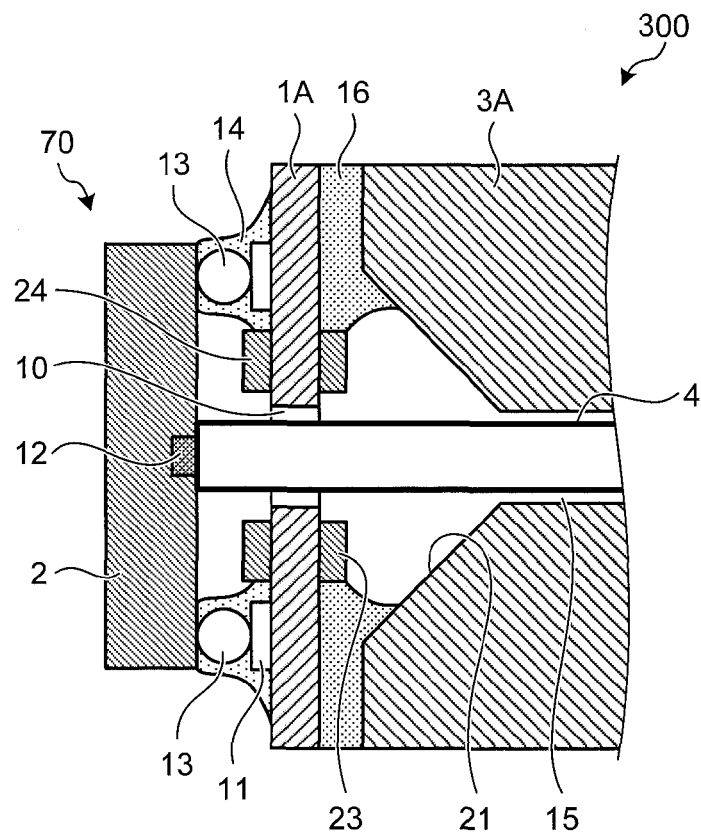
FIG. 10 is a cross-sectional view of an optical transmission module according to a third embodiment.
Figure 11:
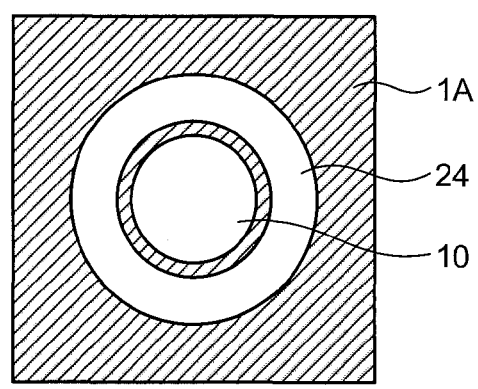
FIG. 11 is a plan view of a hole in a board of the optical transmission module in FIG. 10 viewed from a surface emitting laser side.

An optical transmission module according to a third embodiment is different from the optical transmission module 100 according to the first embodiment in that a projected member is formed around a hole in a board. Hereinafter, the optical transmission module according to the third embodiment is described with reference to the drawings. FIG. 10 is a cross-sectional view of an optical transmission module 300 according to the third embodiment. FIG. 11 is a plan view of a hole 10 in a board 1A of the optical transmission module 300 in FIG. 10 viewed from a surface emitting laser 2 side. Note that the optical transmission module 300 in FIG. 10 includes an optical element module 70 and an optical fiber 4; however, in the same way as the optical transmission module 100 according to the first embodiment, it is also possible to configure such that an optical element module 30 is connected to another end face of the optical fiber 4.

In the optical transmission module 300 according to the third embodiment, a projected member 23 and a projected member 24 are formed around the hole 10 in the board 1A. The projected member 23 constitutes a short cylindrical shape formed around the hole 10 of the board 1A on the mounting side of a guide holding member 3A. The projected member 24 constitutes a short cylindrical shape formed around the hole 10 of the board 1A on the mounting side of the surface emitting laser 2. Inner diameters of the projected member 23 and the projected member 24 are the same as or slightly larger than a diameter of the hole 10. FIG. 11 is a plan view of the hole 10 in the board 1A of the optical transmission module 300 in FIG. 10 viewed from the surface emitting laser 2 side. By forming the projected member 23 into the same shape as the projected member 24 and at the same position relative to the hole 10, a plan view of the hole 10 in the board 1A of the optical transmission module 300 viewed from the guide member 3A side becomes the same as FIG. 11 (the projected member 24 is replaced with the projected member 23). The projected member 23 and the projected member 24 are formed by a resist and the like, and are formed into an intended shape by applying the resist on a surface of the board 1A and by using a photolithography process.

In the third embodiment, mounting of the guide holding member 3A on the board 1A is performed by, after applying the adhesive 16 on an outer periphery of the projected member 23, which is a mounting surface of the board 1A, mounting the guide holding member 3A on the board 1A on which the adhesive 16 is applied by a device such as a bonder, and hardening the adhesive 16. By forming the projected member 23 around the hole 10 of the board 1A on the mounting side of the guide holding member 3A, even in a case where a large amount of the adhesive 16 is applied, it is possible to prevent the adhesive 16 from protruding into the hole 10 since the adhesive 16 is dammed by the projected member 23, and the adhesive 16 flows into the taper 21 of the guide holding member 3A, whereby insertion of the optical fiber 4 can be performed without any problem. Accordingly, a yield rate in manufacturing of the optical transmission module 300 can be improved.

Further, in the third embodiment, mounting of the surface emitting laser 2 on the board 1A is performed by forming an Au bump 13 on a connection surface with the board 1A of the surface emitting laser 2, and by disposing it upon a connection electrode 11 of the board 1A and joining by an ultrasonic device, and by pouring an adhesive 14 into a joining portion, and by hardening the adhesive 14. By forming the projected member 24 around the hole 10 in the board 1A on the mounting side of the surface emitting laser 2, the projected member 24 dams the adhesive 14. Accordingly, it is possible to prevent protrusion of the adhesive 14 inside the hole 10, and the insertion of the optical fiber 4 can be performed without any problem. A yield rate in manufacturing the optical transmission module 300 can be improved.

Figure 12:
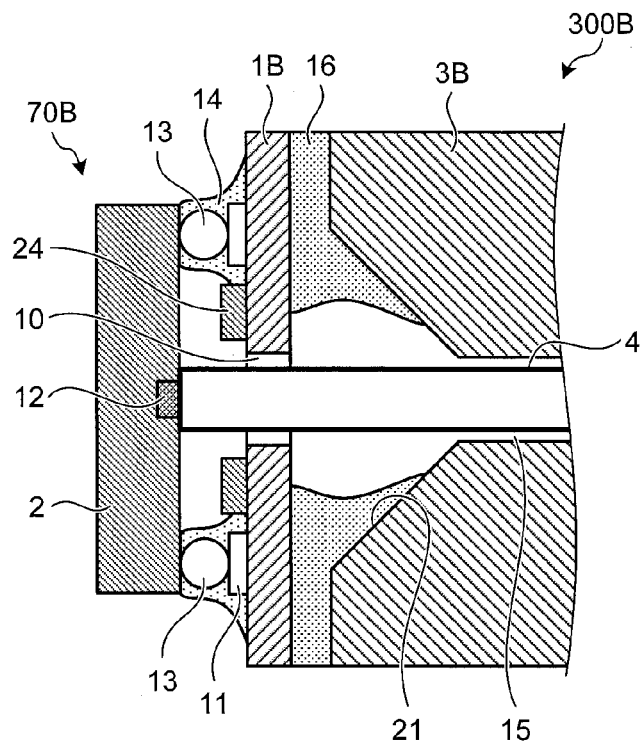
FIG. 12 is a cross-sectional view of an optical transmission module according to Modification 1 of the third embodiment.

Furthermore, as Modification 1 of the optical transmission module 300 according to the third embodiment, an optical transmission module 300B illustrated in FIG. 12 is exemplified. In the optical transmission module 300B of Modification 1, the projected member 24 is formed only around the hole 10 of a board 1B on the mounting surface of the surface emitting laser 2. In Modification 1, by forming the projected member 24 around the hole 10 on the mounting surface of the surface emitting laser 2, it is possible to prevent protrusion of the adhesive 14 inside the hole 10, and to perform insertion of the optical fiber 4 without any problem. Furthermore, in the through hole 15 of the guide holding member 3B, the taper 21 is formed on a side adjacent to the board 1B, whereby the protrusion of the adhesive 16 into the hole 10 can be prevented.

Figure 13:
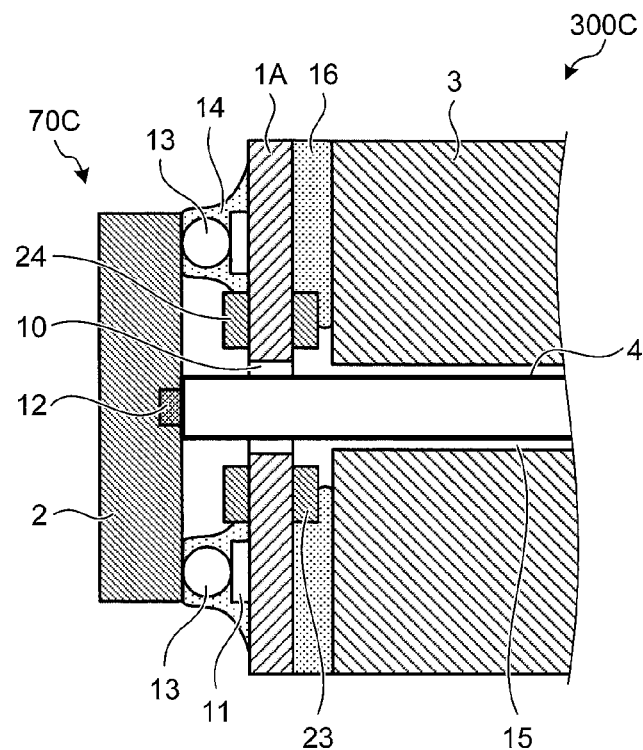
FIG. 13 is a cross-sectional view of an optical transmission module according to Modification 2 of the third embodiment.

Furthermore, as Modification 2 of the optical transmission module 300 according to the third embodiment, an optical transmission module 300C illustrated in FIG. 13 is exemplified. In the optical transmission module 300C according to Modification 2, the projected member 23 and the projected member 24 are formed around the hole 10 of the board 1A. Furthermore, in Modification 2, no taper is formed in the through hole 15 of the guide holding member 3 on the board 1A side. In Modification 2, by forming the projected member 24 around the hole 10 on the mounting surface of the surface emitting laser 2, it is possible to prevent protrusion of the adhesive 14 inside the hole 10, and to perform insertion of the optical fiber 4 without any problem. Furthermore, by forming the projected member 23 around the hole 10 on the mounting surface of the guide holding member 3, it is possible to prevent protrusion of the adhesive 16 inside the hole 10, to perform insertion of the optical fiber 4 without any problem. Note that the same effect can be obtained by forming the projected member 23 around the through hole 15 of the guide holding member 3.

Figure 14:
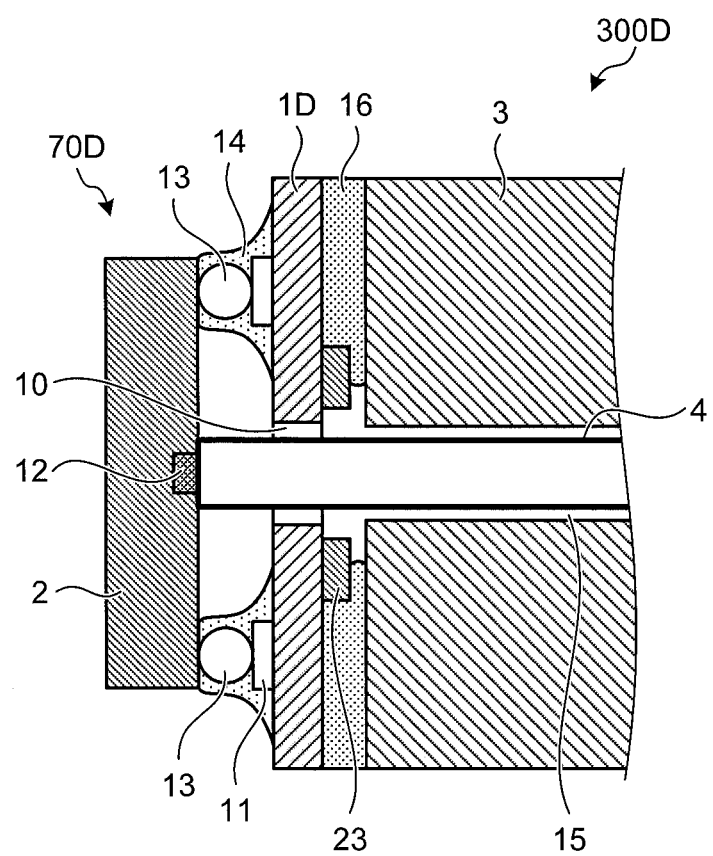
FIG. 14 is a cross-sectional view of an optical transmission module according to Modification 3 of the third embodiment.

Further, as Modification 3 of the optical transmission module 300 according to the third embodiment, an optical transmission module 300D illustrated in FIG. 14 is exemplified. In the optical transmission module 300D according to Modification 3, the projected member 23 is formed only around the hole 10 of a board 1D on a mounting surface of the guide holding member 3. In Modification 3, by forming the projected member 23 around the hole 10 on the mounting surface of the guide holding member 3, it is possible to prevent protrusion of the adhesive 16 inside the hole 10, and to perform insertion of the optical fiber 4 without any problem. Note that in the same way as Modification 2, the same effect can be obtained by forming the projected member 23 around the through hole 15 of the guide holding member 3.

Fourth Embodiment

Figure 15:
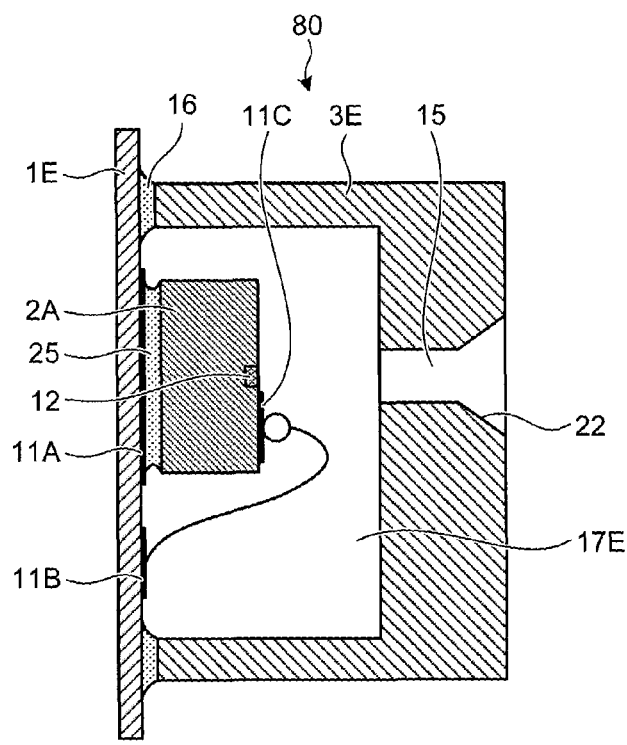
FIG. 15 is a cross-sectional view of an optical element module according to a fourth embodiment.
Figure 16:
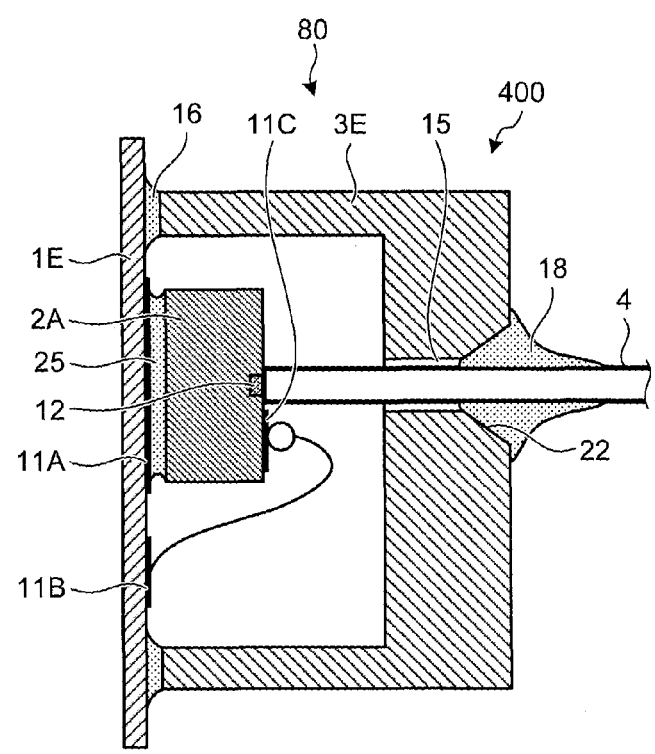
FIG. 16 is a cross-sectional view of an optical transmission module in which an optical fiber is inserted into and fixed to an optical element module according to FIG. 15.

An optical transmission module 400 according to a fourth embodiment uses, as an optical element, a wire bonding type surface emitting laser, which is mounted on a board such that a light emitting unit is positioned to be opposite to the mounting surface of the board. FIG. 15 is a cross-sectional view of an optical element module 80 according to the fourth embodiment. FIG. 16 is a cross-sectional view of the optical transmission module 400 in which an optical fiber 4 is inserted into and fixed to the optical element module 80 in FIG. 15. Note that the optical transmission module 400 in FIG. 16 includes the optical element module 80 and the optical fiber 4; however, it is also possible to configure such that an optical element module 30 is connected to another end face of the optical fiber 4 in the same way as the optical transmission module 100 according to the first embodiment.

On a board 1E, a connection electrode 11A and a connection electrode 11B are formed. On the connection electrode 11A, a conductive adhesive 25 such as an Ag paste or a solder paste is applied. A surface emitting laser 2A is disposed such that a light emitting unit 12 positions opposite to a mounting surface of the board 1E, and by heating a conductive adhesive 25, the surface emitting laser 2A is die-bonded to the connection electrode 11A. On the light emitting unit 12 side of the surface emitting laser 2A, a connection electrode 11C is formed, and the connection electrode 11C and the connection electrode 11B are wire bonded by an Au wire and the like. The wire bonded part may be reinforced by a resin adhesive as necessary.

A guide holding member 3E has a space 17E inside which the surface emitting laser 2A is housed, and is mounted on a mounting surface of the surface emitting laser 2A of the board 1E. After the adhesive 16 is applied to the board 1E, the guide holding member 3E is mounted on the adhesive 16 by a bonder and the like, and the guide holding member 3E is mounted by hardening the adhesive 16. In mounting the guide holding member 3E on the board 1E, a dual-view optical system is used to align a center of the light emitting unit 12 of the surface emitting laser 2 and a center of the through hole 15 in mounting.

Mounting of the optical fiber 4 to the optical element module 80 is performed through the through hole 15. The through hole 15 has a cylindrical shape and substantially the same diameter as an outer diameter of the optical fiber 4. On an insertion side of the optical fiber 4 of the through hole 15, a taper 22 is formed. The optical fiber 4 is inserted into the through hole 15 through the taper 22 to reach the vicinity of the light emitting unit 12, and is joined to the guide holding member 3E by an adhesive 18 at a position where light output from the light emitting unit 12 can be input efficiently. When the optical fiber 4 is joined to the optical element module 80, it becomes the optical transmission module 400 according to the fourth embodiment. In the optical transmission module 400 according to the fourth embodiment, by forming the taper 22 on the insertion side of the optical fiber 4 of the through hole 15, insertion of the optical fiber 4 into the through hole 15 can be performed easily. Furthermore, since the optical fiber 4 and the guide holding member 3E are joined by supplying the adhesive 18 inside the taper 22, a joining area of the guide holding member 3E and the optical fiber 4 can be made larger, whereby a joining strength can be improved.

The optical transmission module 400 according to the fourth embodiment is mounted by integrating the surface emitting laser 2A and the guide holding member 3E on one side surface of the board 1E. Accordingly, manufacturing of the optical transmission module 400 having a high flexibility of design becomes possible.

As above, the embodiments of the present invention have been described; however, the present invention may include various embodiments and the like not described herein, and it is possible to implement various design changes and the like within a scope that does not deviate from the technical ideas specified in claims.

According to some embodiments, in an optical element module having an optical element and a board on which the optical element is mounted, a guide holding member having a through hole into which an optical fiber is configured to be inserted and the optical element are mounted and arranged to be aligned with each other in a thickness direction of the board. The optical fiber is inserted into the cylindrical through hole having substantially the same diameter as an outer diameter of the optical fiber. A distance between an end face of the optical fiber to be inserted and the light emitting unit or the light receiving unit is adjusted for joining. With this, it is possible to achieve miniaturization of the optical element module, and to improve optical transmission efficiency.

As described above, an optical element module, an optical transmission module, and a method of manufacturing the optical transmission module according to the present invention is suitable for use in performing a high-speed signal transmission between an imaging device with a high pixel number and a signal processing device. Furthermore, the optical transmission module according to the present invention is especially suitable for use in which a high-speed data communication is performed and miniaturization is demanded, such as in an endoscope and in an ultrasonic image system (ultrasonic endoscope).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical element module comprising:
   an optical element having a light receiving unit configured to input an optical signal or a light emitting unit configured to output an optical signal;
   a board on which the optical element is mounted; and
   a guide holding member that has a through hole into which an optical fiber including a core and a cladding is configured to be inserted for inputting and outputting the optical signal to or from the light receiving unit or the light emitting unit of the optical element, and is mounted and arranged to be aligned with the optical element in a thickness direction of the board; and
   an adhesive disposed between the board and the guide holding member, the guide holding member being mounted on the adhesive on the board, the adhesive being hardened to fix the guide holding member to the board;

wherein the through hole has a cylindrical shape and has substantially the same diameter as an outer diameter of the optical fiber,
a diameter of the light receiving unit or the light emitting unit is smaller than that of the core of the optical fiber;
the optical element is flip-chip mounted on the board such that the light emitting unit or the light receiving unit is opposed to the board;
the guide holding member is mounted on a surface of the board opposite to where the optical element is mounted;
the board has a hole for transmitting and receiving the optical signal between the optical element and the optical fiber positioned on different surfaces;
an inner diameter of the hole is equal to or larger than an inner diameter of the through hole; and
the through hole includes an end portion facing the board and having a tapered shape.

2. The optical element module according to claim 1, wherein an end portion of the through hole on an insertion opening side of the optical fiber has a tapered shape.

3. The optical element module according claim 1, further comprising a projected member that projects from a mounting surface of the board where the optical element is mounted and that is formed around the hole on the mounting surface of the board.

4. The optical element module according to claim 1, wherein a space is provided between an end face of the through hole on a side of the optical element and the light emitting unit or the light receiving unit for adjusting a distance between an end face of the optical fiber to be inserted and the light emitting unit or the light receiving unit.

5. An optical transmission module using the optical element module according to claim 1, further comprising an optical fiber inserted into the through hole, wherein
the optical fiber is joined to the guide holding member by optically aligning one end face of the optical fiber with the light emitting unit or the light receiving unit of the optical element.

6. The optical transmission module according to claim 5, further comprising:
a transmission module having a light emitting unit optically aligned with the other end face of the optical fiber and configured to output an optical signal to the light receiving unit of the optical element, or
a receiving module having a light receiving unit configured to input the optical signal from the light emitting unit of the optical element.

7. A method of manufacturing the optical transmission module of claim 5, the method comprising:
mounting the optical element on a surface of the board;
mounting the guide holding member having the through hole which has a cylindrical shape and has substantially the same diameter as an outer diameter of the optical fiber, on the board after mounting the optical element on the board, by aligning a center of the light receiving unit or the light emitting unit with a center of the through hole and by arranging the guide holding member to be aligned with the optical element in a thickness direction of the board;
inserting the optical fiber into the through hole;
adjusting a distance between the one end face of the optical fiber and the light receiving unit or the light emitting unit and optically aligning the one end face of the optical fiber with the light emitting unit or the light receiving unit; and
joining the optical fiber to the guide holding member.

8. An optical element module comprising:
an optical element having a light receiving unit configured to input an optical signal or a light emitting unit configured to output an optical signal;
a board on which the optical element is mounted;
a guide holding member that has a through hole into which an optical fiber including a core and a cladding is configured to be inserted for inputting and outputting the optical signal to or from the light receiving unit or the light emitting unit of the optical element, and is mounted and arranged to be aligned with the optical element in a thickness direction of the board; and
an adhesive disposed between the board and the guide holding member to fix the guide holding member to the board,
wherein the through hole has a cylindrical shape and has substantially the same diameter as an outer diameter of the optical fiber;
a diameter of the light receiving unit or the light emitting unit is smaller than that of the core of the optical fiber;
the optical element is flip-chip mounted on the board such that the light emitting unit or the light receiving unit is opposed to the board;
the guide holding member is mounted on a surface of the board opposite to where the optical element is mounted;
the board has a hole for transmitting and receiving the optical signal between the optical element and the optical fiber positioned on different surfaces; and
the optical element module further comprising a projected member disposed between the adhesive and the hole, the projecting member projecting from a mounting surface of the board where the guide holding member is mounted to prevent the adhesive from protruding into the hole.

9. The optical element module according to claim 8, wherein the projected member has an inner diameter and an outer diameter, the inner diameter of the projected member being at least a same diameter as a diameter of the hole.

* * * * *